US00PP13993P39

(12) United States Plant Patent
Austin

(10) Patent No.: US PP13,993 P3
(45) Date of Patent: Jul. 22, 2003

(54) SHRUB ROSE PLANT NAMED 'AUSROMEO'

(75) Inventor: David C. H. Austin, Wolverhampton (GB)

(73) Assignee: David Austin Roses Limited, Albrighton (GB)

( * ) Notice: Subject to any disclaimer, the term of this patent is extended or adjusted under 35 U.S.C. 154(b) by 0 days.

(21) Appl. No.: 10/029,462

(22) Filed: Dec. 20, 2001

(65) Prior Publication Data

US 2003/0121081 P1 Jun. 26, 2003

(51) Int. Cl.[7] ..... A01H 5/00
(52) U.S. Cl. ..... Plt./108
(58) Field of Search ..... Plt./108, 102, 140, Plt./151

(56) References Cited

PUBLICATIONS

UPOV–ROM GTITM Computer Database 2002/03, GTI Jouve Retrieval Software, Citation for Rosa 'Ausromeo'.*

* cited by examiner

*Primary Examiner*—Bruce R. Campell
*Assistant Examiner*—June Hwu
(74) *Attorney, Agent, or Firm*—Klarquist Sparkman LLP

(57) ABSTRACT

Shrub rose plant having blooms of velvety crimson which gradually change to a rich purple; deeply cupped blooms which open out to a shallow, quartered and very full cup; strong, branching growth; and strong old rose fragrance.

1 Drawing Sheet

GENUS AND SPECIES

*Rosa hybrida.*

VARIETAL DENOMINATION

'AUSROMEO'.

SUMMARY OF THE INVENTION

The present invention relates to a new and distinct variety of rose plant of the shrub class which was originated by me by crossing an unnamed seedling (unpatented), with the variety 'AUSbloom,' (U.S. Plant Pat. No. 8,677).

BACKGROUND OF THE INVENTION

The primary objective of this breeding was to produce a new rose variety having a very free-flowering and healthy variety with flowers of the classic English rose shape with a good fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Blooms of velvety crimson which gradually change to a rich purple;

2. Deeply cupped blooms which open out to a shallow, quartered and very full cup;

3. Strong, branching growth; and

4. Strong old rose fragrance.

Asexual reproduction of this new variety by budding on *Rosa dumetorum laxa* rootstock, as performed at Albrighton, England, shows that the foregoing and all other characteristics and distinctions come true to form and are established and transmitted through succeeding propagations.

COMPARISION WITH PARENTS

'AUSromeo' differs from its seed parent in that 'AUSromeo' has dark, reddish purple flowers while the seed parent has crimson red flowers, and differs from its pollen parent in that 'AUSromeo's' flowers have 120 petals and are flat whereas 'AUSbloom's' flowers have 140 petals which are slightly recurved when mature.

COMPARISON WITH SIMILAR VARIETY

The most similar variety, 'AUSverse' (U.S. Plant Pat. No. 13,315) is bushy and upright with dark mat green foliage, whereas 'AUSromeo' is strong, branching and has medium mat green foliage.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (Unpatented).

*Pollen parent.*—'AUSbloom' (U.S. Plant Pat. No. 8,677).

FLOWER

Observations made from plants of five years of age grown in a garden/greenhouse environment at Albrighton, England, in July, 2000.

Blooming habit: Recurrent.

Bud:

*Size.*—About 1 inch long when the petals start to unfurl.

*Form.*—The bud form is pointed ovoid.

*Color.*—When sepals first divide, bud color is: Upper surface: Red-Purple Group 59C. Lower surface: Red-Purple Group 64B. When half blown, the upper sides of the petals are Red-Purple Group 71A; and the lower sides of the petals are Red-Purple Group 72A.

*Sepals.*—Color: Yellow-Green Group 144B with Red Group 47A blush. Length: 0.6 inches. Width: 0.5–0.75 inches. Overall Shape: Lanceolate Apex Shape: Acuminate Surface texture: Smooth with slightly serrated edges on appendaged sepals. There are three lightly appendaged sepals. There are two unappendaged sepals with hairy edges.

*Receptacle.*—Color: Yellow-Green Group 144B. Shape: Funnel. Size: Medium (abot 0.3–0.4 inches long×0.3–0.4 inches wide). Surface: Glandular.

*Peduncle.*—Length: Short, averaging about 2 inches. Surface: Very slightly prickly. Color: Yellow-Green Group 146A with Greyed-Purple Group 184A blush. Strength: Stiff, bending.

Bloom:

*Size.*—Medium. Average open size is 3.5 inches.

*Borne.*—Singly and in flat clusters of up to four blooms.

*Stems.*—Strength: Strong. Average length is about 20–25 inches.

*Form.*—When first open: Cupped. Permanence: Out petals curl back.

*Petalage.*—Number of petals under normal conditions: 120.

*Color.*—The upper sides of the petals are Red-Purple Group 71A. The reverse sides of the petals are Red-Purple Group 71A. The base of each petal is Yellow Group 2C. The major color on the upper side is Red-Purple Group 71A.

*Discoloration.*—The general tonality at the end of the first day: Red-Purple Group 71A. At the end of the third day: Red-Purple Group 70A. As flower ages further color lightens.

*Fragrance.*—Strong, Old Rose.

Petals:

*Texture.*—Smooth.

*Shape.*—Rounded at tip (centre petals).

*Size.*—Length: 4 cm. Width: 5 cm.

*Margin.*—Frilled.

*Apex shape.*—Round.

*Base shape.*—Round.

*Form.*—Tips of outer petals very slightly recurved. Center petals are heavily quilled.

*Arrangement.*—Quartered, imbricated. No petaloids are present but tightly curled petals are present.

*Petaloids.*—Average number: 21. Size: 4 mm width×8 mm height. Color: Red Group RHS 45B. Shape: Elliptical.

*Persistence.*—Petals hang on and dry.

*Lastingness.*—On the plant: Long (about fourteen days). As a cut flower: Fair (about seven days).

Reproductive parts:

*Stamens.*—Number: 50. Anthers: Size: 3/32 inch. Color: Yellow Group 13B. Arrangement: Mixed with petaloids. Filaments: Color: Yellow Group 5C. Pollen: Color: Yellow Group 13C.

*Pistils.*—Number: 100. Styles: Color: Green-Yellow Group 1C. Length: 0.3 inch. Stigmas: Color: Red Group 47B. Length: 1/32 inch.

*Hips.*—Repeats flowers too long to have hips.

Plant:

*Form.*—Shrub (English).

*Growth.*—Vigorous, branching.

*Mature plant.*—Height: 3.5 feet; Width: 2.5 feet

*Rootstock.*—'Dr. Huey' recommended for the United States.

Foliage: Number of leaflets on normal mid-stem leaves: 5.

*Size.*—Medium (6 inches long×2.5 inches wide).

*Quantity.*—Abundant.

*Color.*—New foliage: Upper side: Yellow-Green Group 137A. Lower side: Yellow-Green Group 137D with tint of Greyed Orange Group 176B. Old foliage: Upper side: Green Group 139A. Lower side: Yellow-Green Group 146A.

Leaflets:

*Size.*—About 2.5 inches long×1.5 inches wide.

*Shape.*—Pointed oval.

*Tip shape.*—Pointed.

*Base shape.*—Obtuse.

*Texture.*—Leathery.

*Edge.*—Serrated.

*Serrations.*—Small.

*Petiole color.*—Yellow-Green Group 146C.

*Petiole rachis.*—Color: Yellow-Green Group 144B. Underside with prickles.

*Auricle shape.*—Goes to a point on both sides.

*Stipules.*—Serrated. Length: About 0.6 inches to 0.8 inches.

*Disease resistance.*—Resistant to mildew, blackspot and rust under normal growing conditions.

*Pest resistance.*—Strong.

Wood:

*New wood.*—Color: Yellow-Green Group 146B with Greyed-Purple Group 183B blush. Bark: Smooth.

*Old wood.*—Color: Yellow-Green Group 144A. Bark: Smooth.

Prickles:

*Quantity.*—On main canes from base: Ordinary. On laterals from main canes: Ordinary.

*Form.*—Hooked downward.

*Size.*—Length: 10 mm. Width: 7 mm.

*Color when young.*—Greyed-Purple Group 185B.

*Color when mature.*—Red-Purple Group 59A.

Small prickles:

*Quantity.*—On main stalks: Many. On laterals: Many.

*Color.*—Greyed-Red Group 182A.

Climate hardiness: Hardy in Zones 4 to 9.

I claim:

1. A new and distinct variety of rose plant of the shrub class, substantially as herein shown and described, characterized particularly by blooms of velvety crimson which gradually change to a rich purple; deeply cupped blooms which open out to a shallow, quartered and very full cup; strong, branching growth; and strong old rose fragrance.

* * * * *

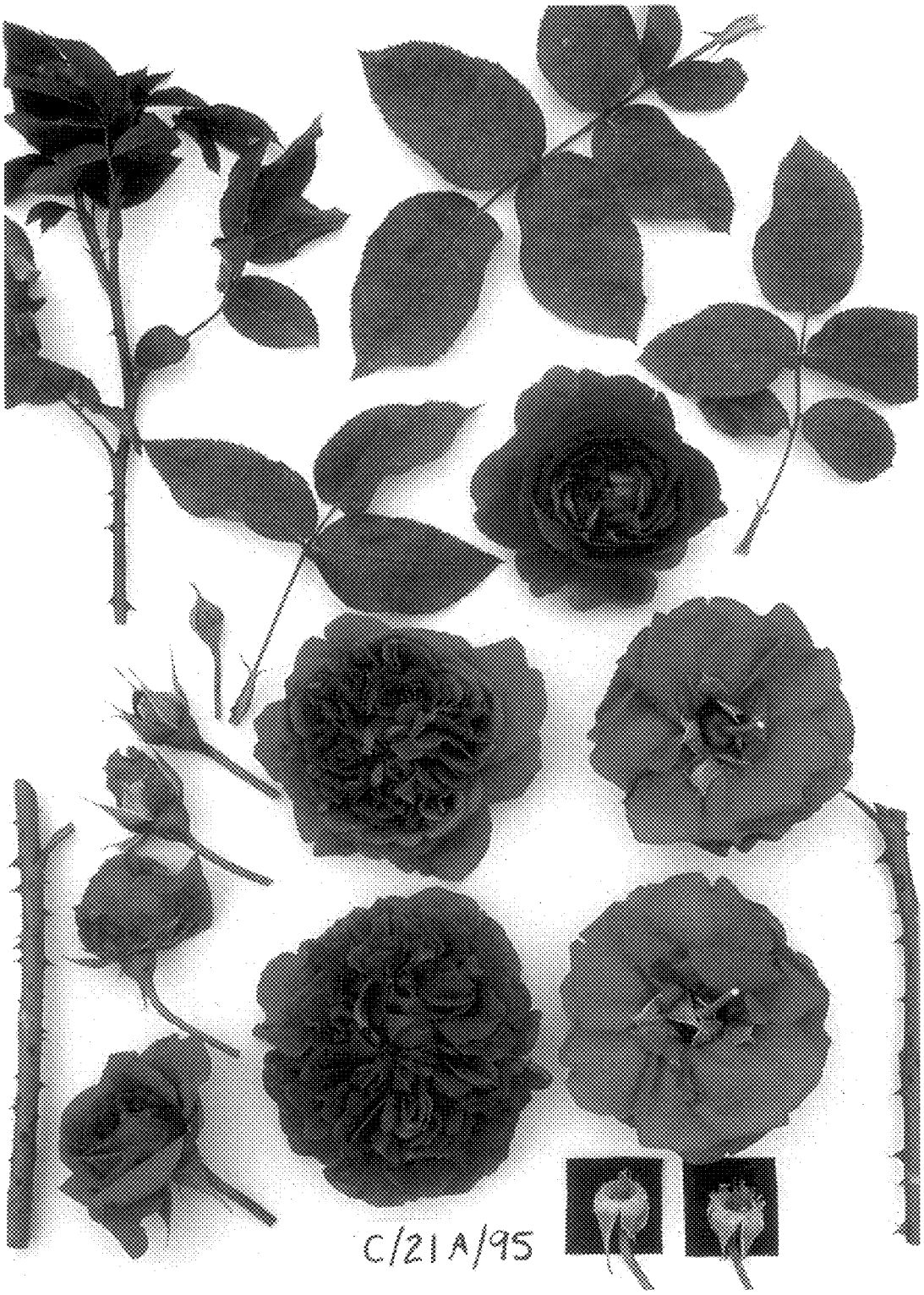
C/21 A/95